United States Patent [19]

Meinert

[11] Patent Number: 5,397,805
[45] Date of Patent: Mar. 14, 1995

[54] TREATMENT LIQUID FOR REAPPLYING (UNFOLDING) DETACHED RETINA TO THE CHORIOID OF THE EYE

[75] Inventor: Hasso Meinert, Ulm, Germany

[73] Assignee: Adatomed Pharmazeutische und Medizintechnische Gesellschaft mbH, Munich, Germany

[21] Appl. No.: 82,529

[22] Filed: Jun. 25, 1993

Related U.S. Application Data

[63] Continuation of Ser. No. 814,891, Dec. 30, 1991, abandoned.

[30] Foreign Application Priority Data

Jan. 3, 1991 [DE] Germany ............... 41 00 059.5

[51] Int. Cl.⁶ ............................................. A61K 47/00
[52] U.S. Cl. ..................................... 514/772; 514/912
[58] Field of Search ............... 514/772, 749, 832, 912, 514/743

[56] References Cited

U.S. PATENT DOCUMENTS 4,366,169 12/1982 White .................. 424/285

FOREIGN PATENT DOCUMENTS

| | | |
|---|---|---|
| 2555408 | 6/1976 | European Pat. Off. . |
| 0089232 | 9/1983 | European Pat. Off. . |
| 0231091 | 8/1987 | European Pat. Off. . |
| 0415263 | 3/1991 | European Pat. Off. . |
| 89/00848 | 2/1989 | WIPO . |

OTHER PUBLICATIONS

Claes et al., "The Use of Perfluorocarbon Liquids in Vitreous Surgery," 1990, pp. 146–150.
Chemical Abstracts, Band 110, Nr. 15, 10. Apr. 1989, Seite 46.
Nabih et al., "Experimental Evaluation of Perfluorophenanthrene as a High Specific Gravity Vitreous Substitute: A Preliminary Report," Band 20, Nr. 4, Apr. 1989.

*Primary Examiner*—Zohreh Fay
*Attorney, Agent, or Firm*—Keck, Mahin & Cate

[57] ABSTRACT

A treatment liquid for unfolding detached retina to the chorioid of the eye containing a PFC-mixture whose PFCs are free from C=C-double bonds and C—H-bonds, with a reduced vapor pressure and a refractive index by virtue of which the PFC/tissue fluid interface is made visible.

23 Claims, 2 Drawing Sheets

TREATMENT LIQUID FOR REAPPLYING (UNFOLDING) DETACHED RETINA TO THE CHORIOID OF THE EYE

This is a continuation of application Ser. No. 07/814,891, filed on Dec. 30, 1991, now abandoned.

The invention concerns a treatment liquid for reapplying (unfolding) detached retina to the chorioid of the eye, containing at least one liquid perfluorocarbon (PFC).

A treatment liquid of that kind is known from U.S. patent specification No. 4 490 351.

The use of liquid perfluorocarbons in the treatment of retina detachment and major tears in the retina has suggested itself in consideration of the high level of chemical stability and densities in the range of 1.5–1.8 $g/cm^3$ of such substances. In retina unfolding, after removal of the vitreous humour, the liquid PFCs are introduced into the eye and, while the patient is lying on his or her back, the liquids, by virtue of their density, press the retina or the retina which is suffering from tears, against the chorioid of the eye again. After a residence time of several hours, the PFC is sucked away again and replaced by another medium, for example methylsilicone oil as the PFCs do not exhibit long-term compatibility That is due to the high density and also the toxicity of the PFCs relative to the eye components. In this connection attention is also directed to the following literature: H. Laqua, K. Lucke, M. H. Foerster 'Entwicklung und gegenwartiger Stand der Silikonolchirurgie' in Klin. Mbl. Augenheilk. 192, 1988, pages 277–283; A. Kampik 'Prophylaxe und Behandlung der proliferativen Vitreoretinopathien' in Z. prakt. Augenheilkd. 7, pages 323–326 (1986); Stanley Chang, Emin Ozmert, Neal J. Zimmerman Intraoperative Perfluorcarbon liquids in the Management of Proliferative Vitreoretinopathy in 'American Journal of Ophthalmology' 106 (December 1988), pages 668–674; Stanley Chang, 'Low Viscosity Liquid Fluorochemicals in Vitreous Surgery' in American Journal of Ophthalmology 103 (January 1987), pages 38–43; Anselm Kampik 'Klinik und Pathogenese der Windenblutenablatio' in Z. prakt. Augenheilkd. 4 (1983), pages 371–378; Klaus Lucke 'Vitreoretinale Chirugie bei komplizierten Netzhautablosungen' in Z. prakt. Augenheilkd. 9 (1988), pages 137–147.

The object of the present invention is to provide a treatment liquid for unfolding detached retina, which contains perfluorocarbons and which has long-term compatibility, that is to say it is non-toxic relative to the eye components involved in the unfolding treatment.

In the treatment liquid for unfolding detached retina, as referred to in the opening part of this specification, that object is attained in accordance with the invention by a perfluorocarbon (PFC) mixture whose PFCs are free from C=C-double bonds and C—H-bonds. The purity of that PFC mixture should be up to 100% of perfluorocarbon.

Highly pure PFCs can preferably be produced by the initial PFC being kept under reflux for several days with a nucleophilic reagent, in particular a secondary amine $R_2NH$ and a strong base, in particular KOH or NaOH. In that case the completely fluorinated compounds do not react. H-bearing and unsaturated PFCs are converted in a sequence of addition and elimination reactions. Depending on the respective position of the double bond the result is a mixture of nitrogen-bearing compounds. In that three-phase system comprising PFC, amines and water, the products formed by reaction with secondary amine go into the amine phase and in that situation can be separated from the unchanged PFCs. Highly toxic N-F compounds break up in accordance with the following equations by reduction by means of iodide ions:

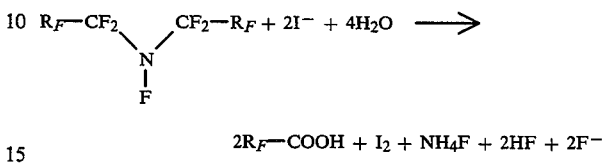

$$2R_F\text{—COOH} + I_2 + NH_4F + 2HF + 2F^-$$

In that way PFCs which have been synthesised in known manner in an ECF or $CoF_3$ process can be purified. For example in the synthesis of perfluorodecaline by $CoF_3$-fluorination of decaline or naphthaline, H-bearing and/or double bond-bearing substances such as $C_{10}F_{18-n}H_n$, $C_{10}F_{16}$, $C_{10}F_{16-n}H_n$ and $C_9F_{16-n}H_n$ are formed as by-products.

By virtue of the above-indicated purifying operation those by-products can be reduced to less than 30 ppm so that it is then no longer possible to detect any toxicity.

Preferably the PFC-mixture contains at least one PFC from the group consisting of perfluorodecaline, perfluorocyclohexylmorpholine, perfluorooctane and perfluorooctylbromide, in a proportion of between 96 and 99.9%, and a proportion of PFCs with low interfacial tension, for which perfluorodimorpholinopropane or perfluorodimorpholinobutane or a perfluorinated tricyclic compound such as perfluoroperhydrophenanthrene are preferably used. The PFC with in particular low interfacial tension is preferably contained in the mixture in a proportion of between 1 and 4%. In addition that provides for a reduction in vapour pressure so that upon vitreous humour replacement, PFC remaining in the eye does not have an excessively high vapour pressure at 37° C. and thus act too strongly on the chorioid. In addition a mixture of that kind provides for a change in the refractive index so that the PFC/tissue fluid interface is clearly visible when carrying out the operation.

PFCs have a very high level of solubility for gases which is of a purely physical nature and thus follows Henry's law. Therefore solubility of gases is proportional at constant temperature to the respective partial pressure of the gas. Solubility also depends on the molecular weight of the gas. The higher the molecular weight, the better is its solubility in PFC. The PFCs which are liquid under normal conditions differ in regard to their solution capability to the effect that their solution capability increases with falling molecular weight. In that respect chain-form PFCs have a still somewhat higher degree of solubility than ring-form PFCs.

Under normal conditions liquid PFCs dissolve between 40 and 55% by volume of oxygen and between 100 and 150% by volume of $CO_2$.

Advantageously therefore it is possible to use dissolved gases in the PFC-mixture, in which case those gases are enriched with a suitable gas, in particular dissolved oxygen, in regard to tissue care in the retina unfolding operation, on the one hand, while on the other hand, in regard to an improved retina unfolding action, by virtue of generating a temporarily higher pressure against the subjacent tissue, they are enriched with a dissolved and in particular chemically inert gas. Gaseous PFCs, such as for example $CF_4$ or $C_2F_6$ or $C_3F_8$ or $C_4F_8$ and also sulfur hexafluoride ($SF_6$) are preferably suitable for that purpose.

Under normal conditions the gaseous PFCs and $SF_6$ are very soluble in liquid PFCs. Like gaseous PFCs, in particular $SF_6$ is used as a gaseous insulator in high-voltage generators and other electrical equipment because of its high molecular weight, its chemically inert nature, its low dielectric constant and its high dielectric strength, while it is used as a temperature insulator on account of its low level of thermal conductivity.

The gaseous PFCs and the $SF_6$ referred to, in the retina unfolding operation, produce a higher pressure in respect of the detached retina, against the subjacent chorioid tissue. That increased pressure can possibly also be applied within an only relatively short period of time. Between 0.5 and 5% by volume, with a maximum of 10% by volume, of added gaseous PFCs or $SF_6$ is sufficient in each case. The increased contact pressure is achieved not only by virtue of the relatively high specific weight of the added gases but also by virtue of their higher vapour pressure in the liquid PFC-mixture. In dependence on the amount of added gaseous PFCs or $SF_6$ and the partial vapour pressures thereof, the higher vapour pressure of the operating medium, in the form of the liquid PFC-mixture, which higher pressure is desired in particular in the first part of the operation phase, can be varied as desired in respect of magnitude over a desired given period of time.

In order to permit retina unfolding over a prolonged period of time and possibly to avoid subsequent tamponning or plugging with silicone oil, in a preferred fashion, use is made of a PFC-emulsion in water, which is optically homogeneous and transparent. Preferably, a suitable surfactant is used in that respect to emulsify the PFC-component. Preferably a non-ionogenic emulsifier is used. Preferably the free emulsifier (surfactant) concentration is between 1 and 3%. A nonionogenic, biocompatible tenside such as for example polyalkyleneglycol based on block polymers of ethylene and propylene oxide, which is known under the Trade Mark 'Pluronic' is preferably suited as a surfactant, in particular when perfluorooctylbromide is used as the PFC.

Depending on whether the PFC-emulsion in water is to be used directly for retina unfolding or for subsequent substitution of the chamber fluid, the density of the emulsion can be adjusted by the proportion of PFC being between 10 and 60% by weight. The PFC-component within that proportion of concentration is variable. As the PFC-component, beside perfluorooctylbromide, it is also possible to use perfluorooctane, perfluorodecaline and perfluorocyclohexylmorpholine, within the specified proportion (between 10 and 60% by weight) of the emulsion in water with a proportion of between 96 and 99.9% by volume and a further proportion of between 1 and 4% by volume of perfluorodimorpholinoalcane, in particular perfluorodimorpholinopropane or perfluorodimorpholinobutane or a perfluorinated tricyclic compound such as perfluoroperhydrophenanthrene, wherein the proportions in % by volume are related to the volume of the PFC-mixture.

In that respect, it is advantageously possible to make use of the high degree of solubility of gases, in particular oxygen, in regard to those PFCs. That provides for an adequate supply of oxygen to the tissue. Preferably it is also possible to add to the emulsions adjuvants, metabolites such as ascorbic acid, retinol, and/or medicaments.

The desired osmotic pressure (osmolarity about 350 nmol/kg) can preferably be adjusted by way of isotonic solutions, in particular physiological salt components. The oncotic pressure (about 4.42 kPa) is preferably adjusted by the addition of hydroxyethyl starch or dextran and/or hyaluronic acid. The desired vapour pressure (at 37° C. about 5.06 kPa) can be achieved for example by the above-mentioned added gaseous PFCs in the emulsion.

The emulsion accordingly contains a suitable buffer system in order to keep the pH constant.

The specific weight of the emulsion is preferably adjusted to be greater than 1 and lower than 1.6. That can be achieved by virtue of the content of the respective PFCs.

The following Table lists examples of various PFC-mixtures which can be used as an unfolding liquid in reapplying detached retina to the chorioid of the eye.

| PFCs | PFC-Mixtures Proportions (% by volume) | | | |
|---|---|---|---|---|
| Perfluorodecaline or | 99% | 98% | 97% | 96% |
| Perfluorocyclohexylmorpholine or | " | " | " | " |
| Perfluorooctane or | " | " | " | " |
| Perfluorooctylbromide | " | " | " | " |
| Perfluorodimorpholinopropane or | 1%(vol) | 2%(vol) | 3%(vol) | 4%(vol) |
| Perfluorodimorpholinobutane or | " | " | " | " |
| Perfluoroperhydrophenanthrene | " | " | " | " |

The mixtures can be produced by means of conventional mixers.

For production of the PFC-emulsion in water, the PFC is homogenised by means of a suitable surfactant, in particular a non-ionogenic, biocompatible surfactant (emulsifier) in a Gaulin homogeniser with water and thereafter the emulsion is filtered in a sterile condition at a pore width of about 400 nanometers.

Set out hereinafter are various examples of optically homogeneous transparent PFC-emulsions in water. A PFC-mixture as indicated in the foregoing Table can be used for the PFC component used in these examples.

The following Table sets out various examples of PFC-emulsions. The proportions are specified in % w/v.

| PFC-component | F-Cyclohexylmorpholine | 20.0 | F-Octylbromide | 50.0 |
|---|---|---|---|---|
| | F-Dimorpholinopropane | 2.0 | | |

-continued

| | | | |
|---|---|---|---|
| Tenside | Pluronic F-68 | 3.0 | 6.0 |
| Oncotic reagents | Hydroxyethyl starch | 3.0 | 3.0 |
| Mineral salts | NaCl | 0.58 | 0.58 |
| | KCl | 0.034 | 0.034 |
| | $CaCl_2$ | 0.020 | 0.020 |
| | $NaHCO_3$ | 0.024 | 0.024 |
| | $MgCl_2$ | 0.02 | 0.02 |
| | Glucose | 0.17 | 0.17 |
| | Ascorbic acid | 0.020 | 0.020 |
| | Urea | 0.04 | 0.04 |
| Water | | ad 100 ml | ad 100 ml |

Figure 1:
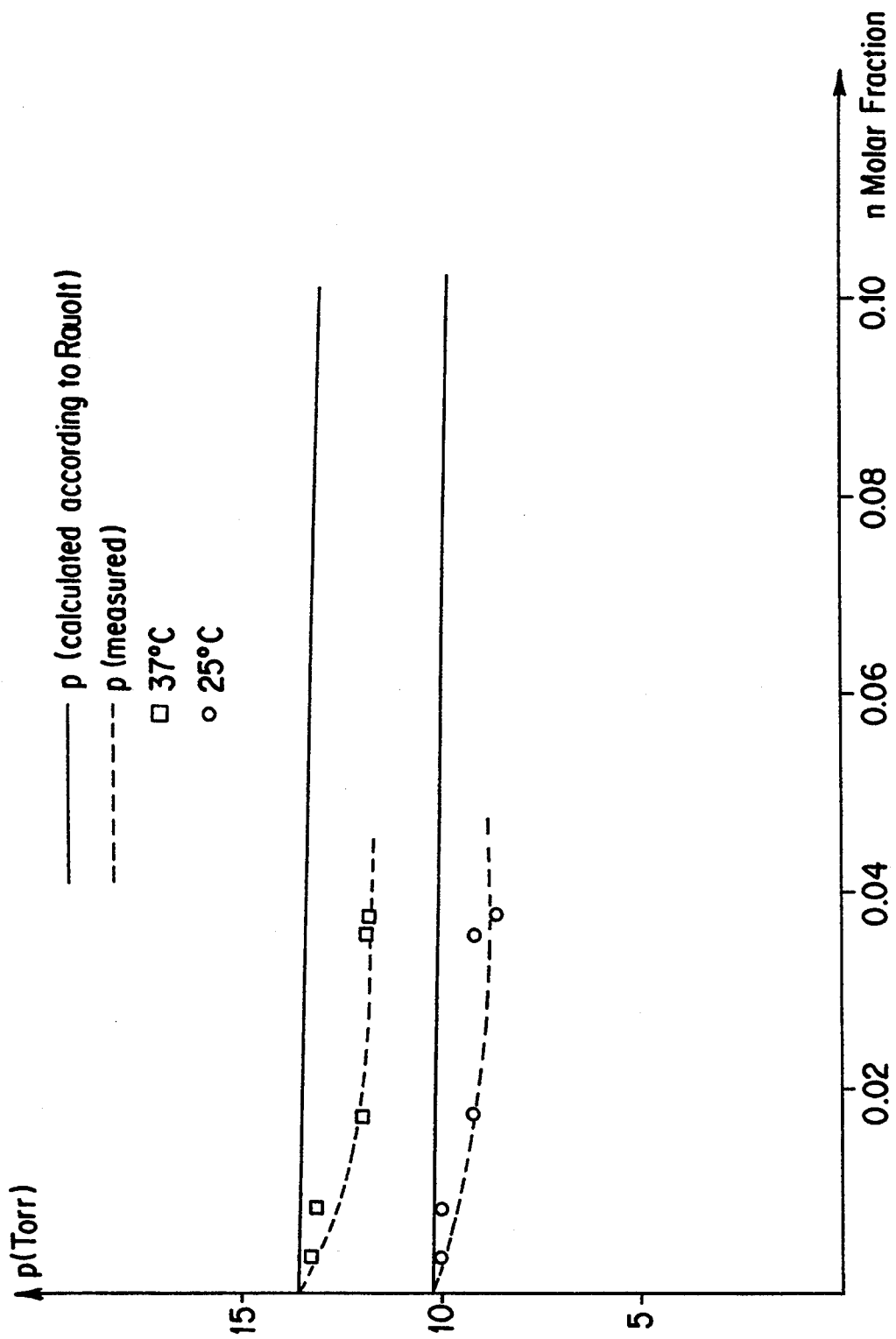
FIG. 1 shows the vapor pressure of F-dimorpholinopropane and perfluorodecaline.
Figure 2:
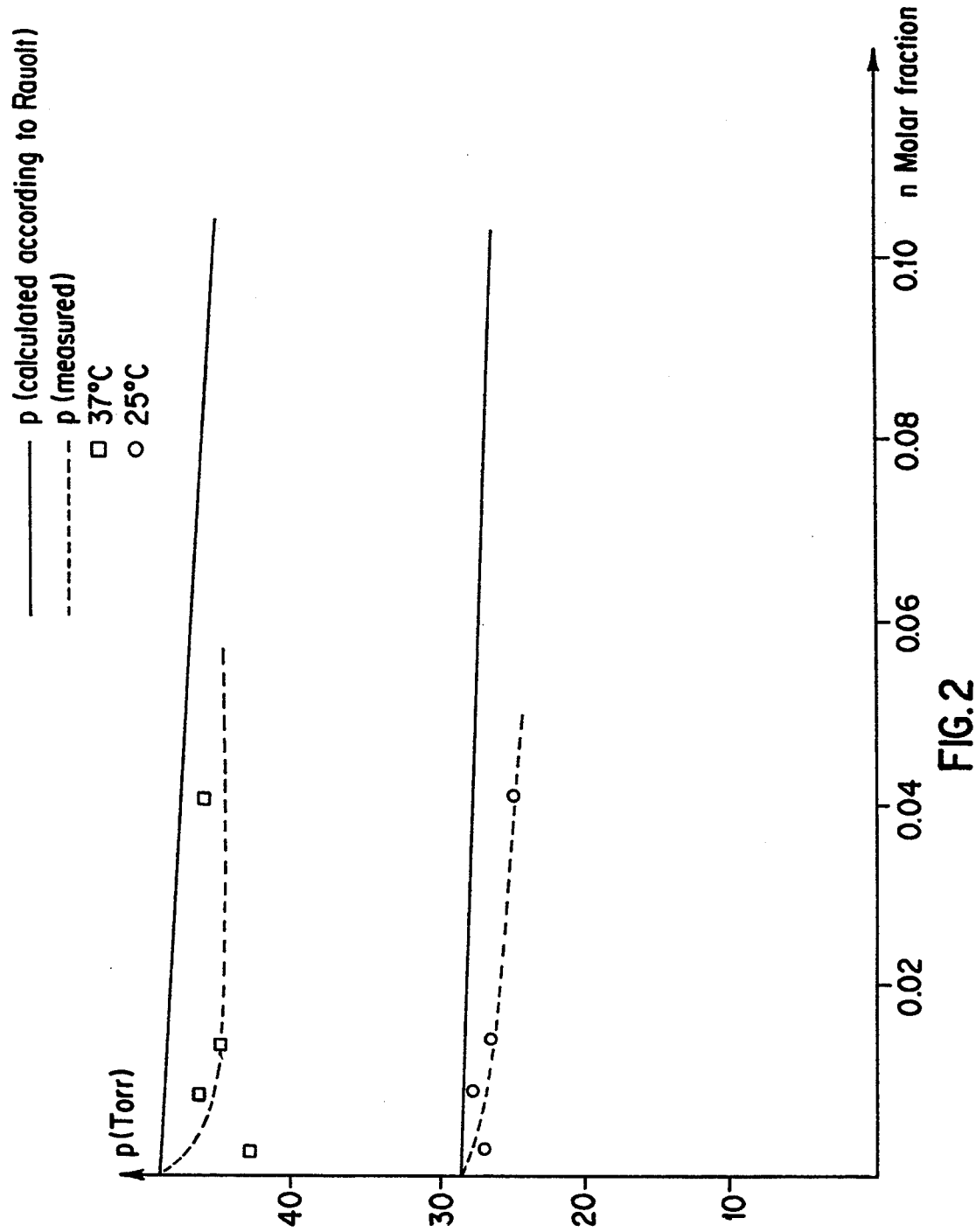
FIG. 2 shows the vapor pressure of F-dimorpholinopropane and perflurooctane.

Tables 1 through 4 below and FIGS. 1 and 2 attached set out vapour pressure curves and refractive indices of F-dimorpholinoalcane/perfluorodecaline and F-dimorpholinopropane/perfluorooctane solutions. The results show that the behaviour of the above-indicated solutions is in all cases not collegative (additivity of the vapour pressures and refractive indices respectively) and consequently these are not ideal solutions, as was hitherto generally assumed in respect of perfluorocarbons. Herein $n_1$ denotes the molar fraction, $P_{25}$ denotes the vapour pressure at 25° C., $p_{37}$ denotes the vapour pressure at 37° C. and $n_D$ denotes the refractive index at 25° C.

TABLE 1

Vapour pressures of F-dimorpholinopropane/perfluorodecaline

| $n_1$ | $p_{25}$ (Torr) | $p_{37}$ (Torr) |
|---|---|---|
| — | 10.22 | 13.6 |
| 0.0038 | 10.05 | 13.27 |
| 0.0086 | 10.10 | 11.96 |
| 0.0180 | 9.16 | 11.82 |
| 0.0364 | 9.14 | 11.82 |
| 0.0382 | 8.53 | 11.70 |
| 1 | 5.72 | 6.30 |

TABLE 2

Vapour pressures of F-dimorpholinopropane/perfluorooctane

| $n_1$ | $p_{25}$ (Torr) | $p_{37}$ (Torr) |
|---|---|---|
| — | 28.36 | 49.40 |
| 0.0031 | 24.84 | 42.95 |
| 0.0092 | 27.66 | 46.53 |
| 0.0148 | 26.31 | 44.80 |
| 0.0420 | 27.24 | 45.83 |
| 1 | 5.72 | 6.30* |

*from the measurements for perfluorodecaline

TABLE 3

Refractive index of F-dimorpholinoalcane/perfluorodecaline

| propane | | butane | | pentane | |
|---|---|---|---|---|---|
| $n_1$ | $n_D^{25}$ | $n_1$ | $n_d^{25}$ | $n_1$ | $n_d^{25}$ |
| — | $1.312_5$ | — | $1.312_5$ | — | $1.312_5$ |
| 0.0106 | $1.312_0$ | 0.0055 | $1.312_1$ | 0.0225 | $1.312_2$ |
| 0.0240 | $1.311_5$ | 0.0137 | $1.311_8$ | 0.0427 | $1.311_9$ |
| 0.0369 | $1.311_8$ | 0.0248 | $1.311_8$ | 0.0864 | $1.311_6$ |
| 0.662 | $1.311_5$ | 0.0439 | $1.311_8$ | — | — |
| 0.1048 | $1.311_3$ | — | — | — | — |

TABLE 4

Refractive index of F-dimorpholinopropane/perfluorooctane

| $n_1$ | $n_D^{25}$ |
|---|---|
| — | 1.272 |
| 0.0057 | 1.272 |
| 0.0179 | 1.273 |

TABLE 4-continued

Refractive index of F-dimorpholinopropane/perfluorooctane

| $n_1$ | $n_D^{25}$ |
|---|---|
| 0.0930 | 1.278 |

I claim:

1. A composition for reapplying a detached retina to the chorioid of an eye, containing a therapeutically effective amount of at least one liquid perfluorocarbon (PFC) characterized by a PFC-mixture wherein said PFCs are purified to be free from free from C=C double bonds and C—H bonds.

2. A composition as set forth in claim 1 characterised in that the PFC-mixture contains at least one PFC from the group consisting of perfluorodecaline, perfluorocyclohexylmorpholine, perfluorooctane and perfluorooctylbromide.

3. A composition as set forth in claim 2 characterised in that the PFC from the group consisting of perfluorodecaline, perfluorocyclohexylmorpholine, perfluorooctane and perfluorooctylbromide is present in a proportion of between 96 and 99.9% by volume.

4. A composition as set forth in claim 1 characterised in that the PFC-mixture has a proportion of between 1 and 4% by volume of a perfluorodimorpholinoalcane or a perfluorinated tricyclic compound.

5. A composition as set forth in claim 4 characterised in that the perfluorinated tricyclic compound is perfluoroperhydrophenanthrene.

6. A composition as set forth in claim 4 characterised in that the alkane is perfluorodimorpholinobutane or perfluorodimorpholinopropane.

7. A composition as set forth in claim 1 characterised in that a gas is dissolved in the PFC-mixture.

8. A composition as set forth in claim 7 characterised in that the dissolved gas serves for tissue care.

9. A composition as set forth in claim 8 characterised in that the gas dissolved in the PFC-mixture is oxygen.

10. A composition as set forth in claim 7 characterised in that the dissolved gas serves to adjust the contact pressure involved in the retina unfolding operation.

11. A composition as set forth in claim 10 characterised in that one or more gaseous PFCs or $SF_6$ are dissolved in the PFC-mixture.

12. A composition as set forth in claim 1 characterised in that it is in the form of a PFC-emulsion in water.

13. A composition as set forth in claim 12 characterised in that the emulsion is adjusted in respect of its osmotic and oncotic pressure to eye vitreous humour conditions.

14. A composition as set forth in claim 12 characterised in that the emulsion is adjusted in respect of its osmotic and oncotic pressure to chamber fluid conditions.

15. A composition as set forth in claim 10 characterised in that the amount of PFC-mixture in the emulsion is between 10 and 60% by weight.

16. A composition as set forth in claim 10 characterised in that the emulsifier is a non-ionogenic emulsifier.

17. A composition as set forth in claim 10 characterised by a free emulsifier concentration of between 1 and 3%.

18. A composition as set forth in claim 10 characterised in that the emulsifier is a non-iogenic biocompatible tenside.

19. A composition as set forth in claim 18 characterised in that the tenside is an ethylene oxide-propylene oxide block polymer or a derivative derived therefrom.

20. A composition as set forth in claim 10 characterised in that the osmotic pressure is adjusted by physiological salt components.

21. A composition as set forth in claim 10 characterised in that the oncotic pressure is adjusted by the addition of at least one substance from the group consisting of hydroxyethyl starch, dextran and hyaluronic acid.

22. A composition as set forth in claim 10 characterised in that the specific weight of the emulsion is greater than 1 and lower than 1.6.

23. A composition for unfolding a detached retina for reapplying to the chorioid of an eye containing a therapeutically effective amount of at least one liquid perfluorocarbon (PFC) wherein said perfluorocarbon is purified to be free from C=C double bonds and C—H bonds by refluxing with a secondary amine and a strong base and separating the products formed by reaction with the secondary amine from the unchanged perfluorocarbon and by reacting produced compounds having H—F bonds with iodide ions.

* * * * *